United States Patent [19]
Gordon

[11] 3,965,262
[45] June 22, 1976

[54] METHOD OF ENHANCING LEARNING AND/OR MEMORY IN WARM BLOODED ANIMALS

[75] Inventor: Paul Gordon, Chicago, Ill.

[73] Assignee: Strategic Medical Research Corporation, Chicago, Ill.

[22] Filed: Apr. 29, 1974

[21] Appl. No.: 465,339

Related U.S. Application Data

[63] Continuation-in-part of Ser. No. 337,134, March 1, 1973, and a continuation-in-part of Ser. No. 424,786, Dec. 14, 1973.

[52] U.S. Cl. .............................. 424/180; 260/210 R
[51] Int. Cl.² ............................................ H01N 9/00
[58] Field of Search .................................... 424/180

[56] References Cited
UNITED STATES PATENTS
3,152,115    10/1964    Morel et al. .................. 424/180

Primary Examiner—Lewis Gotts
Assistant Examiner—Cary Owens
Attorney, Agent, or Firm—L. S. Van Landingham, Jr.

[57] ABSTRACT

The present invention provides a novel method of enhancing learning and/or memory in warm blooded animals. This is accomplished by administering an ffective amount to enhance the ability of the animal to learn tasks, or to enhance the ability of the animal to memorize information of at least one ethereally monosubstituted monosaccharide having the general formula $S_1 - \underline{O} - Y$, and/or at least one ethereal monosubstitution of monosaccharide derivatives having the general formula $S_2 - \underline{O} - Y$, and/or organic acid and inorganic acid salts thereof, as defined hereinafter. The warm blooded animal is subjected to an environment wherein it is required to learn tasks and/or memorize information and it is capable of learning tasks and memorizing information at markedly increased rates.

34 Claims, No Drawings

METHOD OF ENHANCING LEARNING AND/OR MEMORY IN WARM BLOODED ANIMALS

RELATED APPLICATIONS

This application is a continuation-in-part of my copending application Ser. No. 337,134, filed on Mar. 1, 1973, for Therapeutic Composition, Novel Compounds Useful Therein and Method of Using the Same, and of my copending application Ser. No. 424,786, filed on Dec. 14, 1973, for Therapeutic Composition, Novel Compounds Useful Therein, and Method Of Using The Same. The disclosures of these applications are incorporated herein by reference.

BACKGROUND OF THE INVENTION

The present invention is broadly related to a novel method of enhancing learning and/or memory in warm blooded animals. In some of its more specific variants, the invention is further concerned with the treatment of various pathologies in warm blooded animals involving learning disabilities, disorientation and memory loss.

The novel antiviral compounds and therapeutic compositions disclosed and claimed in my aforementioned earlier filed copending applications Ser. Nos. 337,134 and 424,786 possess striking antiviral properties and are highly effective in treatment of a wide spectrum of viral infections in humans and other lower warm blooded animals. It has now been discovered that these novel compounds and therapeutic compositions have still other unusual and unexpected therapeutically valuable properties.

For example, surprisingly the novel compounds and therapeutic compositions markedly enhance the ability of warm blooded animals to learn tasks and/or to memorize information. The rate of learning and the retention of the learned information are increased markedly. It is also possible to initiate learning under conditions where it otherwise would not occur at a satisfactory rate. Thus, the novel compounds and therapeutic compositions may be administered to children or young animals having learning and/or memory disabilities in general, including such categories as minimal brain dysfunction, mental retardation, and the like.

The novel compounds and therapeutic compositions also improve the performance of aged humans and other aged lower warm blooded animals. The method of the invention is especially useful in treating those functions which deteriorate with age, and especially recent memory functions and learning disabilities. Thus, the novel compounds and therapeutic compositions may be used in the treatment of the stigmata of aging in the human central and/or autonomic nervous systems, and more specifically, to treat the senile brain syndrome, Alzheimer's disease, Jakob-Kreuzfeldt's disease, and pathologies in general involving disorientation, learning disabilities and/or memory loss.

A large number of other pathologies in immature or adult humans and other lower warm blooded animals which involve disorientation, learning disabilities, and/or memory loss may be treated by the method of the invention. For example, insofar as both neurotic and psychotic states in humans may relate to or receive contributions from learning or memory disabilities, such human pathologies may be treated with the compounds and therapeutic compositions described herein.

It is an object of the present invention to provide a novel method of enhancing the ability of warm blodded animals to learn tasks and/or to memorize information.

It is a further object to provide a novel method of increasing the rate of learning and the retention of learned information in warm blooded animals.

It is still a further object to provide a novel method of improving the capacity of the central nervous system and/or the autonomic nervous system in warm blooded animals to respond favorably to outside stimuli.

It is still a further object to provide a novel method of enhancing the performance of aged warm blooded animals in learning tasks and retaining learned information, and treating the stigmata of aging in the central and/or autonomic nervous systems.

It is still a further object to provide a novel method of treating various pathologies in warm blooded animals involving learning disabilities, disorientation, and/or memory loss.

Still other objects and advantages of the invention will be apparent to those skilled in the art upon reference to the following detailed description.

DETAILED DESCRIPTION OF THE INVENTION INCLUDING PREFERRED VARIANTS THEREOF

In practicing the method of the invention, the ability of a warm blooded animal to learn tasks and/or to memorize information are enhanced by administering thereto an effective amount of at least one ethereally monosubstituted monosaccharide having the general formula $S_1$—O—Y, and/or at least one ethereal monosubstitution of monosaccharide derivatives having the general formula $S_2$—O—Y, and/or organic acid and inorganic acid salts thereof. In the foregoing general formulae, $S_1$ is the residue of a nonderivatized monosaccharide selected from the group consisting of pentoses, hexoses and heptoses, and $S_2$ is the residue of a monosaccharide selected from the group consisting of pentoses, hexoses and heptoses which has been derivatized with (a) one or more aliphatic alcohols containing 1–18 carbon atoms and preferably 1–4 carbon atoms to produce an acetal group at one or more available hydroxyl residua, (b) one or more aldehydes containing 1–18 carbon atoms and preferably 1–4 carbon atoms to produce single or multiple acetal groups at one or more available hydroxyl residua, (c) one or more ketones containing 1–18 carbon atoms and preferably 1–4 carbon atoms to produce single or multiple ketal groups at one or more available hydroxyl residua, or (d) one or more organic acid residua containing 1–18 carbon atoms and preferably 1–4 carbon atoms to produce ester groups at one or more available hydroxyl residua. In each instance, Y is selected from the group consisting of cyclic monovalent nitrogen-containing organic radicals and residua and monovalent organic radicals and residua having the general formula

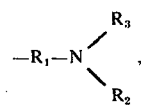

wherein $R_1$ is a divalent organic radical having a linear carbon chain length of about 1–7 carbon atoms and $R_2$ and $R_3$ are selected from the group consisting of —H, —OH, —SH, halogen and monovalent organic radicals and residua having a linear carbon chain length of about 1–7 carbon atoms. When $R_2$ or $R_3$ is halogen, the halogen may be F, Cl, Br or I, of which Cl and Br is usually preferred. The organic radical $R_1$, and $R_2$ and $R_3$ when they are organic radicals, may be branched or unbranched linear carbon chains and may be saturated or unsaturated, and, when saturated, the linear and/or branched carbon chains may contain one or more double or triple carbon-to-carbon bonds. The linear and/or branched carbon chains of $R_1$, $R_2$ and $R_3$ may be substituted or unsubstituted and, when substituted, one or more substituents may be present, such as —OH, —SH, halogen (F, Cl, Br and/or I), branched or unbranched and saturated or unsaturated hydrocarbon radicals containing 1–7 and preferably 1–3 carbon atoms, —$OR_4$ and/or —$SR_4$ radicals wherein $R_4$ is a branched or unbranched and saturated or unsaturated hydrocarbon radical containing 1–7 and preferably 1–3 carbon atoms, carboxylic acid residua containing 1–7 and preferably 1–3 carbon atoms, and amino groups and aminohydrocarbon radicals containing 1–7 and preferably 1–3 carbon atoms. Preferably, $R_1$ is a hydrocarbon radical having a linear carbon chain length of 1–3 or 1–4 carbon atoms and $R_2$ and $R_3$ are individually selected from the group consisting of hydrogen and/or hydrocarbon radicals having linear carbon chain lengths of 1–3 or 1–4 carbon atoms.

Examples of compounds from which cyclic organic radicals and residua are derived include (a) monovalent nitrogen containing saturated, unsaturated or aromatic carbocyclic compounds containing about 4–8 carbon atoms in the ring and preferably about 5–6 carbon atoms in the ring and at least one nitrogen atom attached thereto or to an organo substituent thereon, (b) heterocyclic organic compounds containing about 3–8 carbon atoms in the ring and at least one ring nitrogen atom and (c) derivatives of the foregoing compounds wherein at least one substituent is present, such as —OH, —SH, halogen (F, Cl, Br and/or I), branched or unbranched and saturated or unsaturated hydrocarbon radicals containing 1–7 and preferably 1–3 carbon atoms, —$OR_5$ and/or —$SR_5$ radicals wherein $R_5$ is a branched or unbranched and saturated or unsaturated hydrocarbon radical containing 1–7 and preferably 1–3 carbon atoms, carbocyclic acid residua containing 1–7 and preferably 1–3 carbon atoms, and amino groups and aminohydrocarbon radicals containing 1–7 and preferably 1–3 carbon atoms.

The nonderivatized monosaccharide residue $S_1$ may exist in an open chain or cyclic form. However, it is usually preferred that $S_1$ have the following general formula:

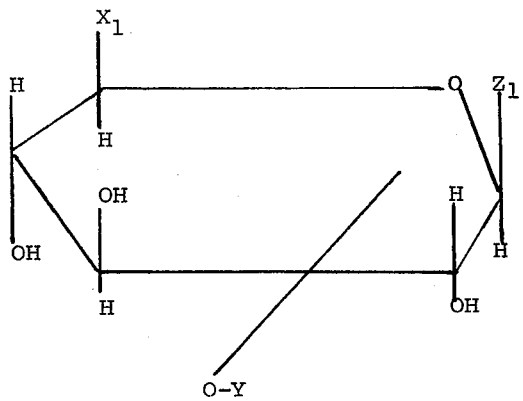

wherein $X_1$ and $Z_1$ are H, OH and/or hydroxyalkyl groups containing up to 2 carbon atoms, Y represents the same organic radicals and residua as aforementioned, and one of the OH groups, $X_1$ or $Z_1$ in the formula is replaced by —O—Y. The above general formula illustrates the hexacyclic form of the various isomers of the pentoses, hexoses and heptoses, the relative spatial configuration of the —H, and —OH groups about the rings, and the monosubstitution thereof in accordance with one presently preferred variant of the invention. The hydroxyl group of the hemiacetal or hemiketal linkage may assume an $\alpha$ or a $\beta$ configuration and the compounds may be in the form of anomers or mixtures of anomers.

The derivatized monosaccharide residue $S_2$ may exist in an open chain or cyclic form having the general formulae:

(a) 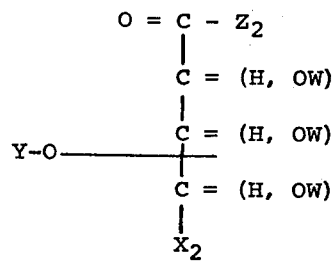

(b) 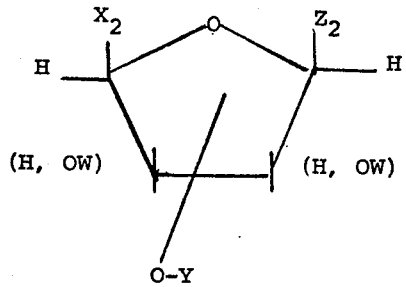

(c) 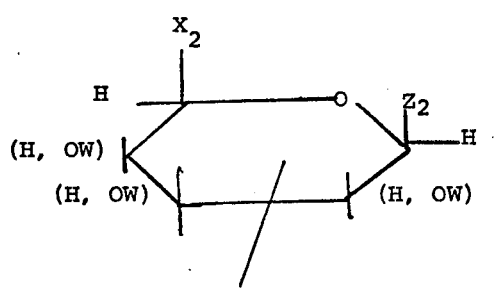

wherein $X_2$ and $Z_2$ are H, OH, hydroxyalkyl, alkoxyl and/or alkoxyalkyl containing up to 3 carbon atoms, W is H, alkyl, alkenyl, cyclic alkane or cyclic aromatic containing 1–18 and preferably 1–6 carbon atoms or acyl containing 1–18 and preferably 1–4 carbon atoms, Y represents the same organic radicals and residua as aforementioned, and one of the OW groups, $X_2$ or $Z_2$ in the formula is replaced by —O—Y. The above general formulae illustrate the various isomers of the pentoses, hexoses and heptoses, the relative spatial configuration of the —H and —OH groups about the ring, and the monosubstitution thereof in accordance with one presently preferred variant of the invention. The hydroxyl or alkoxyl residue of the hemiacetal or hemiketal linkage may assume an α or a β configuration and the compounds may be in the form of anomers or mixtures of anomers.

The configurations of the various derivatives of isomers of the aforementioned pentoses, hexoses and heptoses are well known to those skilled in this art and numerous reference books are available on the subject, the teachings of which are incorporated herein by reference. For example, see the *Textbook of Biochemistry* 4th Edition, by West et al. (1966) and *The Monosaccharides* by Stanek, Cerny, Kocourek and Pacak (1963). The prior art discloses, for example, a total of eight open chain isomers for the reducing hexoses, and an even larger number of open chain isomers for the reducing heptoses. Either the D-series or the L-series of the pentoses, hexoses and heptoses may be used in practicing the invention, but it is usually preferred to use the D-series. The hexoses often given the best results and especially D-talose, D-galactose, L-galactose, D-idose, D-gulose, D-mannose, D-glucose, L-glucose, D-altrose and D-allose. The aforementioned pentoses, hexoses and heptoses may be ethereally monosubstituted in any available position and derivatized at one or more of the remaining hydroxyl groups. Nevertheless, it is understood that substitution of certain positions of specific monosaccharide derivatives results in more therapeutically active or less toxic compounds. For instance, substitution of the 1-O- and 3-O-positions of glucose and the 6-O- position of galactose results in especially valuable compounds. Additionally, substitution of the 3-O- position of 1,2-O-isopropylidene-D-glucofuranose or 1,2:5,6-di-O-isopropylidene-D-glucofuranose and the 6-O- position of 1,2-O-isopropylidene-D-galactopyranose or 1,2:3,4-di-O-isopropylidene-D-galactopyranose also results in especially valuable compounds.

The following substituents may be ethereally substituted on any of the available positions of the various isomers of the pentoses, hexoses and heptoses to produce nontoxic compounds having exceptional therapeutic activity for the purposes of the present invention:

-(n-propylamino),
-(N',N'-dimethylamino-n-propyl),
-(N',N'-dimethylaminoisopropyl),
-(N'-methylpiperidyl),
-(N',N'-dimethylaminoethyl),
-(N',N'-diethylaminoethyl),
-(2',N',N'-trimethylamino-n-propyl),
-dimethylamino,
-(N',N'-dimethylaminomethyl),
-(N',N'-dimethylaminopropyl),
-(N',N'-dimethylamino-iso-butyl),
-(N',N'-dimethylamino-n-butyl),
-(N',N'-dimethylamino-iso-pentyl),
-(N',N'-dimethylaminopentyl),
-(N'-methylamino-n-propyl),
-(N'-methyl-N'-ethylamino-n-propyl),
-(N',N'-diethylamino-n-propyl),
-(amino-n-propyl),
-(N'-ethylamino-n-propyl),
-(N'-propylamino-n-propyl),
-(N',N'-iso-propylamino-n-propyl),
-(1',2'-ethylamino-n-propyl),
-(1'-n-propylpyrrolidyl),
-(1'-n-propylpiperidyl),
-piperidyl,
-(N',N'-dimethylamino-sec-butyl).

Of the foregoing substituents, -(N',N'-dimethylamino-n-propyl) is presently preferred and especially when substituted in the 1-O- or 3-O- position of glucose or in the 6-O- position of galactose, or when substituted in the 3-O- position of 1,2-O-isopropylidene-D-glucofuranose or 1,2:5,6-di-O-isopropylidene-D-glucofuranose or the 6-O- position of 1,2-O-isopropylidene-D-galactopyranose or 1,2:3, 4-di-O-isopropylidene-D-galactopyranose.

The following compounds of the general formula $S_1$—O—Y have been found to have exceptional activity and are presently preferred for use in the method of the invention:

3-O-3'-(n-propylamino)-D-glucose,
3-O-3'-(N',N'-dimethylamino-n-propyl)-D-glucose,
3-O-4'-(N-methyl piperidyl)-D-glucose,
3-O-2'-(N',N'-dimethylaminoethyl)-D-glucose,
3-O-2'-(N',N'-diethylaminoethyl)-D-glucose,
3-O-3'-(2',N',N'-trimethylamino-n-propyl)-D-glucose
α-N',N'-dimethylaminoisopropyl-D-glucoside,
6-O-3'-(N',N'-dimethylamino-n-propyl)-D-galactose,
3-O-2'-(N',N'-dimethylaminopropyl)-D-glucose,
6-O-2'-(N',N'-dimethylaminopropyl)-D-galactose, and organic acid and inorganic acid salts thereof.

Of the foregoing compounds, 3-O-3'-(N',N'-dimethylamino-n-propyl)-D-glucose is presently preferred.

Additional compounds of the general formula $S_1$—O—Y, wherein Y is

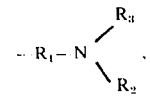

which may be used in practicing the invention are listed below:

| Monosaccharide Residue ($S_1$) | Substituent (Y) | | |
| --- | --- | --- | --- |
| | $R_1$ | $R_2$ | $R_3$ |
| 3-O-D-Glucose | 3'-n-propyl | H | methyl |
| " | " | ethyl | " |
| " | " | H | ethyl |
| " | 2'-n-propyl | methyl | methyl |
| " | 3'-1,2-propenyl | " | " |
| " | sec.-butyl | " | " |
| " | 3'-butyl | " | " |
| " | 2'-ethyl | H | H |
| " | methyl | H | H |
| 6-O-D-Galactose | 3'-n-propyl | H | methyl |
| " | " | ethyl | " |
| " | " | H | ethyl |
| " | 3'-1,2-propenyl | methyl | methyl |
| " | sec.-butyl | " | " |
| " | 3'-butyl | " | " |

Still other compounds of the general formula $S_1$—O—Y, wherein Y is a cyclic monovalent nitrogen containing organic radical or residue, which may be used in practicing the invention are as follows:

| Monosaccharide Residue ($S_1$) | Substituent (Y) | |
|---|---|---|
| | Cyclic Radical | Substituent on the Cyclic Radical |
| 3-O-D-Glucose | 4'-piperidyl | H |
| " | 3'-piperidyl | methyl, H |
| " | 2'-piperidyl | " " |
| " | 3'-pyrrolidyl | " " |
| " | 2'-pyrrolidyl | " " |
| 6-O-D-Galactose | 4'-piperidyl | H |
| " | 3'-piperidyl | methyl, H |
| " | 2'-piperidyl | " " |
| " | 3'-pyrrolidyl | " " |
| " | 2'-pyrrolidyl | " " |

Novel compounds of the general formula $S_1$—O—Y of exceptional activity may be defined generically as follows:

3-O-3'-(N',N'-dimethylamino-n-propyl)-glucose,
3-O-4'-(N-methyl piperidyl)-glucose,
3-O-2'-(N',N'-dimethylaminoethyl)-glucose
3-O-3'-(2',N',N'-trimethylamino-n-propyl)-glucose,
α-N',N'-dimethylaminoisopropyl-glucoside,
6-O-3'-(N',N'-dimethylamino-n-propyl)-galactose,
3-O-2'-(N',N'-dimethylaminopropyl)-glucose,
6-O-2'-(N',N'-dimethylaminopropyl)-galactose, and
organic acid and inorganic acid salts thereof.

Species of the foregoing novel compounds which are presently preferred are as follows:

3-O-3'-(N',N'-dimethylamino-n-propyl)-D-glucopyranose,
3-O-4'(N-methyl piperidyl)-D-glucopyranose,
3-O-2'-(N',N'-dimethylaminoethyl)-D-glucopyranose,
3-O-3'-(2',N',N'-trimethylamino-n-propyl)-D-glucopyranose,
α-N',N'-dimethylaminoisopropyl-D-glucoside,
6-O-3'-(N',N'-dimethylamino-n-propyl)-D-galactopyranose,
3-O-2'(N',N'-dimethylaminopropyl)-D-galactopyranose,
6-O-2'-(N',N'-dimethylaminopropyl)-D-galactopyranose, and
organic acid and inorganic acid salts thereof.

The following compounds of the general formula $S_2$—O—Y have been found to have exceptional activity and are presently preferred for use in the method of the invention:

3-O-3'-(n-propylamino)-1,2-O-isopropylidene-D-glucofuranose,
3-O-3'-(N',N'-dimethylamino-n-propyl)-1,2-O-isopropylidene-D-glucofuranose,
3-O-4'-(N'-methylpiperidyl)-1,2-O-isopropylidene-D-glucofuranose,
3-O-2'-(N',N'-dimethylaminoethyl)-1,2-O-isopropylidene-D-glucofuranose,
3-O-2'-(N',N'-diethylaminoethyl)-1,2-O-isopropylidene-D-glucofuranose,
3-O-3'-(2',N',N'-trimethylamino-n-propyl)-1,2-O-isopropylidene-D-glucofuranose,
3-O-2'-(N',N'-dimethylaminopropyl)-1,2-O-isopropylidene-D-glucofuranose,
6-O-3'-(N',N'-dimethylamino-n-propyl)-1,2-O-isopropylidene-D-galactopyranose,
6-O-2'-(N',N'-dimethylaminopropyl)-1,2-O-isopropylidene-D-galactopyranose,
3-O-3'-(n-propylamino)-1,2:5,6-di-O-isopropylidene-D-glucofuranose,
3-O-3'-(N',N'-dimethylamino-n-propyl)-1,2:5,6-di-O-isopropylidene-D-glucofuranose,
3-O-4'-(N'-methylpiperidyl)-1,2:5,6-di-O-isopropylidene-D-glucofuranose,
3-O-2'-(N',N'-dimethylaminoethyl)-1,2:5,6-di-O-isopropylidene-D-glucofuranose,
3-O-2'-(N',N'-diethylaminoethyl)-1,2:5,6-di-O-isopropylidene-D-glucofuranose,
3-O-3'-(2',N',N'-trimethylamino-n-propyl)-1,2:5,6-di-O-isopropylidene-D-glucofuranose,
3-O-2'-(N',N'-dimethylaminopropyl)-1,2:5,6-di-O-isopropylidene-D-glucofuranose,
6-O-3'-(N',N'-dimethylamino-n-propyl)-1,2:3,4-di-O-isopropylidene-D-galactopyranose,
6-O-2'-(N',N'-dimethylaminopropyl)-1,2:3,4-di-O-isopropylidene-D-galactopyranose,
α-N',N'-dimethylamino-iso-propyl-2,3:5,6-di-O-isopropylidene-D-glucofuranoside, and organic and inorganic acid salts thereof.

Of the foregoing compounds, 3-O-3'-(N',N'-dimethylamino-n-propyl)-1,2-O-isopropylidene-D-glucofuranose is presently preferred.

Additional compounds of the general formula $S_2$—O—Y, wherein Y is

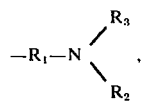

which may be used in practicing the invention are listed below:

| Monosaccharide Residue ($S_2$) | Substituent (Y) | | |
|---|---|---|---|
| | $R_1$ | $R_2$ | $R_3$ |
| 3-O-1,2-O-isopropylidene-D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O-1,2-O-isopropylidene-D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |
| 3-O-1,2:5,6-di-O-isopropylidene-D-glucofuranose | 3'-n-propyl | H | methyl |
| " | " | ethyl | " |
| " | " | H | ethyl |
| " | 2'-iso-propyl | methyl | methyl |
| " | 3'-1,2-propenyl | " | " |
| " | sec-butyl | " | " |
| " | 3'-butyl | " | " |
| " | 2'-ethyl | H | H |
| " | methyl | H | H |
| 6-O-1,2:3,4-di-O-isopropylidene-D-galactopyranose | 3'-n-propyl | H | methyl |
| " | " | ethyl | " |
| " | " | H | ethyl |
| " | 3'-1,2-propenyl | methyl | methyl |
| " | 2'-iso-propyl | " | " |
| " | sec-butyl | " | " |
| " | 3'-butyl | " | " |
| " | 2'-ethyl | H | H |
| " | methyl | H | H |

Still other compounds of the general formula $S_2$—O—Y, wherein Y is a cyclic monovalent nitrogen-containing organic radical or residue, which may be used in practicing the invention, are as follows:

| Monosaccharide Residue ($S_2$) | Substituent (Y) | |
|---|---|---|
| | Cyclic Radical | Substituent on the Cyclic Radical |
| 3-O-1,2-O-isopropylidene-D-glucofuranose | 4'-piperidyl | H |
| '' | 3'-piperidyl | methyl, H |
| '' | 2'-piperidyl | '' '' |
| '' | 3'-pyrrolidyl | '' '' |
| '' | 2'-pyrrolidyl | '' '' |
| 6-O-1,2-O-isopropylidene-D-galactopyranose | 4'-piperidyl | H |
| '' | 3'-piperidyl | methyl, H |
| '' | 2'-piperidyl | '' '' |
| '' | 3'-pyrrolidyl | '' '' |
| '' | 2'-pyrrolidyl | '' '' |
| 3-O-1,2:5,6-di-O-isopropylidene-D-glucofuranose | 4'-piperidyl | H |
| '' | 3'-piperidyl | methyl, H |
| '' | 2'-piperidyl | '' '' |
| '' | 3'-pyrrolidyl | '' '' |
| '' | 2'-pyrrolidyl | '' '' |
| 6-O-1,2:3,4-di-O-isopropylidene-D-galactopyranose | 4'-piperidyl | H |
| '' | 3'-piperidyl | methyl, H |
| '' | 2'-piperidyl | '' '' |
| '' | 3'-pyrrolidyl | '' '' |
| '' | 2'-pyrrolidyl | '' '' |

Novel compounds of the general formula $S_2$—O—Y having exceptional activity may be defined generically as follows:

3-O-3'-(N',N'-dimethylamino-n-propyl)-1,2-O-isopropylideneglucofuranose,

3-O-4'-(N'-methylpiperidyl)-1,2-O-isopropylideneglucofuranose,

3-O-2'-(N',N'-dimethylaminoethyl)-1,2-O-isopropylideneglucofuranose,

3-O-3'-(2',N',N'-trimethylamino-n-propyl)-1,2-O-isopropylideneglucofuranose,

3-O-2'-(N',N'-dimethylaminopropyl)-1,2-O-isopropylideneglucofuranose,

6-O-3'-(N',N'-dimethylamino-n-propyl)-1,2-O-isopropylidenegalactopyranose,

6-O-2'-(N',N'-dimethylaminopropyl)-1,2-O-isopropylidenegalactopyranose,

3-O-3'-(N',N'-dimethylamino-n-propyl)-1,2:5, 6-di-O-isopropylideneglucofuranose, 3-O-4'-(N'-methylpiperidyl)-1,2:5, 6-di-O-isopropylideneglucofuranose, 3-O-2'-(N',N'-dimethylaminoethyl)-1,2:5, 6-di-O-isopropylideneglucofuranose, 3-O-3'-(2',N',N'-trimethylamino-nn-propyl)-1, 2:5, 6-di-O-isopropylideneglucofuranose, 3-O-2'-(N',N'-dimethylaminopropyl)-1,2:5, 6-di-O-isopropylideneglucofuranose, 6-O-3'-(N',N'-dimethylamino-n-propyl)-1, 2:3,4-di-O-isopropylidenegalactopyranose, 6-O-2'-(N',N'-dimethylaminopropyl)-1,2:3, 4-di-O-isopropylidenegalactopyranose, 6-O-2'-(N',N'-dimethylaminopropyl)-1, 2:3, 4-di-O-isopropylidenegalactopyranose, -N',N'-dimethylamino-iso-propyl-2, 3:5,6-di-O-isopropylideneglucofuranoside, and organic and inorganic acid salts thereof.

Species of the foregoing novel compounds which are presently preferred are as follows:

3-O-3'-(N',N'-dimethylamino-n-propyl)-1, 2-O-isopropylidene-D-glucofuranose,

3-O-4'-(N'-methylpiperidyl)-1,2-O-isopropylidene-D-glucofuranose,

3-O-2'-(N',N'-dimethylaminoethyl)-1, 2-O-isopropylidene-D-glucofuranose,

3-O-3'-(2',N',N'-trimethylamino-n-propyl)-1, 2-O-isopropylidene-D-glucofuranose, 3-O-2'-(N',N'-dimethylaminopropyl)-1, 2-O-isopropylidene-D-glucofuranose, 6-O-3'-(N',N'-dimethylamino-n-propyl)-1, 2-O-isopropylidene-D-galactopyranose, 6-O-2'-(N',N'-dimethylaminopropyl)-1, 2-O-isopropylidene-D-galactopyranose, 3-O-3'-(N',N'-dimethylamino-n-propyl)-1, 2:5,6-di-O-isopropylidene-D-glucofuranose, 3-O-4'-(N'-methylpiperidyl)-1,2:5, 6-di-O-isopropylidene-D-glucofuranose, 3-O-3'-(2',N', N'-trimethylamino-n-propyl)-1,2:5,6-di-O-isopropylidene-D-glucofuranose, 3-O-2'-(N',N'-dimethylaminoethyl)-1, 2:5, 6-di-O-isopropylidene-D-glucofuranose, 3-O-2'-(N,N'-dimethylaminopropyl)-1, 2:5,6-di-O-isopropylidene-D-glucofuranose, 6-O-3'-(N',N'-dimethylamino-n-propyl)-1, 2:3,4-di-O-isopropylidene-D-galactopyranose, 6-O-2'-(N',N'-dimethylaminopropyl)1,2:3,4-di-O-isopropylidene-D-galactopyranose, -N',N'-dimethylamino-iso-propyl-2, 3:5,6-di-O-isopropylidene-D-glucofuranoside, and organic and inorganic acid salts thereof.

In general, the preparation of compounds of the formula $S_1$—O—Y described herein involves the formation of alkyl ethers or substituted alkyl ethers at selected positions on the desired nondrivatized monosaccharide, such as at position 1-O- or 3-O- of D-glucose, position 6-O- of D-galactose, and position 3-O- of D-fructose. Similarly, the preparation of compounds of the formula $S_2$—O—Y described herein involves the formation of alkyl ethers or substituted alkyl ethers at selected positions on the desired monosaccharide derivative, such as at position 3-O- of 1,2-O-isopropylidene-D-glucofuranose or 1,2:5,6-di-O-isopropylidene-D-glucofuranose, position 6-O- of 1, 2-O-isopropylidene-D-galactopyranose or 1,2:3,4-di-O-isopropylidene-D-galactopyranose, and position 3-O- of 1,2-O-isopropylidene-D-fructopyranose or 1,2:5, 6-di-O-isopropylidene-D-fructopyranose. The condensation of the substituent substrate with the desired nonderivatized monosaccharide or the monosaccharide derivative at the desired position may be achieved by various prior art techniques. One method is described in U.S. Pat. No. 2,715,121, issued Aug. 9, 1955, to GLEN, et al., the disclosure of which is incorporated herein by reference. The method described in this patent requires extreme reaction conditions and often gives low yields. The product purity is also less than satisfactory.

The preferred method of preparation involves much milder reaction conditions than employed in U.S. Pat. No. 2,715,121. The side reactions are minimized, the purity of the final product is greatly improved and the method may be adapted to a series of solvents having varying properties such as dioxane, tetrahydrofuran and benzene. Briefly, the improved method involves the reaction of a monosaccharide derivative which is blocked with one or more organo groups in the hydroxyl group positions adjacent the desired position to be substituted. The blocked monosaccharide is dissolved in one of the foregoing solvents and is reacted with a halogenated organo amino compound having the desired carbon chain length and configuration in the presence of a base such as sodium hydroxide. The resulting products are compounds of the formula $S_2$—O—Y, which are blocked derivatives of the compounds $S_1$—O—Y of the invention. Selective removal of one or more blocking groups may be accomplished by hydrolysis under specific conditions resulting in a new product which is to be considered a compound suitable for use in this invention. The reaction of either the blocked compound or the hydrolyzed compound with any organic or inorganic acid to form a salt thereof or with any organic or inorganic base to form a salt thereof also results in a compound suitable for use in this invention.

It is understood that simple derivatives of the compounds described herein may be used in practicing the invention. Such derivatives may be prepared by prior art techniques and procedures and used as an ingredient in the therapeutic composition and method of the invention.

For example, the free amine compounds are basic and form organic acid salts and inorganic acid salts, and the resulting salts are useful in the method of the invention. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, acetic acid, alkylcarboxylic acids, oxalic acid, tartaric acid, lactic acid, pyruvic acid, malic acid, succinic acid, gluconic acid and glucuronic acid. The aqueous solution of the resulting salt is evaporated to the volume necessary to assure precipitation of the salt upon cooling. The precipitated salt is recovered by filtration, washed and dried to obtain a final amine salt product. The amine salts are often preferred for use in formulating the therapeutic compositions of the invention as they are crystalline and relatively nonhydroscopic. The amine salts are also better adapted for intramuscular injection than are the free amines.

Prior art blocking techniques may be employed such as acetonization and acetylation. Suitable prior art blocking methods are described in the aforementioned U.S. Pat. No. 2,715,121 and are described in the specific examples appearing hereinafter. In instances where an aldehyde or ketone is reacted with hydroxyl groups on adjacent carbon atoms, the initial compound may be dissolved in the desired adehyde or ketone under anhydrous conditions and a Lewis acid catalyst is added in a catalytic quantity, such as 1% zinc chloride or anhydrous phosphoric acid. Often acetone is the preferred blocking agent, but aldehydes or ketones of much higher molecular weight may be used when desired such as those containing up to 25 carbon atoms. The reaction mixture is agitated at room temperature for a prolonged reaction period, such as 24–48 hours. The compound may be blocked in a plurality of positions, such as the 1,2- and 5,6- positions. It is usually preferred to block positions such as the 1,2- positions as the resulting partially blocked compound is much less toxic than compounds blocked in all available hydroxyl groups.

It is also possible to block one or more free hydroxyl positions of the compound with an ester group, wherein the carboxylic acid residue contains 1–18 and preferably 1–3 carbon atoms. The ester derivatives likewise may be prepared following prior art techniques such as by reacting a carboxylic acid anhydride with the compound following prior art practices. Additionally, the $\alpha$ or $\beta$ alkyl derivatives of nonderivatized monosaccharides or of monosaccharide derivatives such as 2,3:5,6-di-O-isopropylidene-D-glucofuranoside may be prepared following prior art techniques. In this latter instance, the compound is dissolved in a dry alcohol having the desired carbon chain length with the aforementioned residua and reacted with the compound in the presence of a catalyst such as the hydrogen chloride of Dowex 5— H+ resin. While the above discussed derivatives are presently preferred, it is understood that still other simple derivatives may be prepared following prior art techniques and then used in practicing the present invention. In addition to the foregoing, the compounds may also include monosubstitutions of monosaccharide derivatives in which the substrate

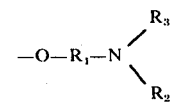

may be replaced by a substituent $R_7$, where $R_7$, is a deoxymonosaccharide derivative of halogen, keto, amino, lower alkyl, mercapto, alkenyl, alkynyl, aromatic, heterocyclic or alkylcarboxylic acid and its derivatives. $R_7$ may also represent the same groups as the above substrate of the monosaccharide derivative ethers. Still other useful compounds have a general formula $S_1$—O—$Y_1$, or $S_2$—O—$Y_1$, wherein $Y_1$ is —$R_8$—S—$R_9$, $R_8$ is a saturated or unsaturated hydrocarbon radical containing 1–7 carbon atoms, $R_9$ is a monovalent saturated or unsaturated hydrocarbon radical containing 1–7 carbon atoms and hydrogen, and $S_1$— and $S_2$— are as previously described.

The compounds of the present invention may be administered to human patient or other warm blooded animal to be treated either orally or by parenteral administration. When the therapeutic composition is to be administered orally, the compound may be admixed with a prior art filler and/or binder such as starch and a disintegrator, and the admixture is pressed into a tablet of a size convenient for oral administration. Capsules also may be filled with the powdered therapeutic composition and administered orally. Alternatively, a water solution or suspension of the therapeutic composition may be admixed with a flavored syrup such as cherry syrup and administered orally. When the therapeutic composition is administered by intramuscular injection, the compound is usually dissolved in a physiological saline solution which contains sodium chloride in sufficient concentration to make the overall solution to be injected isotonic to body fluids. A salt of the free amine compound is usually preferred in instances where the compound is administered by intramuscular injection. In treating some patients or when convenient, the salt form of the compound in aqueous solution may also be administered by nasopharyngeal spray. Administration also may be by means of a suppository in patients unable to retain medication administered by mouth.

The dosage may be varied over extremely wide limits, as the compounds are effective at low dosage levels and are relatively free of toxicity and adverse side effects.

The compounds may be administered in the minimum quantity which is therapeutically effective, and the dosage may be increased as desired up to the maximum dosage tolerated by the patient. Animal toxicity data indicate that the limiting nontoxic dosage may be up to 100–200 times the minimum effective dosage. Also, it is not necessary to carefully control the dosage for patients sensitive to the prior art learning enhancing drugs. As a general rule, the compound may be administered in an amount of about 1–250 milligrams per kilogram of body weight per day, and preferably in an amount of about 25–100 milligrams per kilogram of body weight per day, over the period required for treatment. In some instances, very good results are obtained at dosage levels of about 2–20 milligrams per kilogram of body weight per day.

The method of the invention is useful in enhancing learning and/or memory in both immature and adult warm blooded animals, and in both normal and abnormal specimens. The compounds have been shown to increase the rate of learning, and initiate learning under conditions where it otherwise would not occur. There is also a marked improvement in the retention of the learned information. As a result, the compounds described herein may be administered to children or adults having learning disabilities and/or poor memory, and especially where there is a minimal grain dysfunction, mental retardation, or similar abnormal conditions. The method of the invention is very effective in treating pathologies in general which involve disorientation, learning disabilities and/or memory loss. In accordance with one variant of the invention, both neurotic and psychotic states in humans may be treated insofar as they relate to or receive contributions from learning disabilities or memory loss.

The method of the invention is especially useful in improving the performance of aged humans and other aged lower warm blooded animals. Functions which deteriorate with age, and especially learning disabilities and/or recent memory functions, may be greatly improved. The method of the invention is very useful in the treatment of the stigmata of aging in the human central and/or autonomic nervous systems. More specifically, the method of the invention may be used in treating senile brain syndrome, Alzheimer's disease, Jakob-Kreuzfeldt's disease, and other similar pathologies due to aging involving disorientation, learning disabilities, and/or memory loss.

The following specific examples further illustrate the present invention.

EXAMPLE 1

To a solution of 104 g (0.4 mole) of 1,2:5,6-di-O-isopropylidene-D-glucofuranose in 550 ml of 1,4-dioxane was added 189.7 g (1.2 mole) of 3-chloro-N',N'-dimethylamino propane in the form of the hydrochloride salt and 144 g (3.6 mole) of sodium hydroxide. The suspension was mechanically stirred and heated to reflux for 18 hours. The reaction mixture thus prepared was filtered, the solids were washed with 1,4-dioxane and the washings were combined with the filtered liquid. The solvent was removed under reduced pressure and an amber-colored viscous oil was obtained.

The oil was distilled under high vacuum (less than 1 mm Hg) while using a very slight dry nitrogen purge to obtain high and low boiling fractions. The low boiling fraction was identified as unreacted 3-chloro-N',N'-dimethylamino propane. The high boiling fraction had a boiling point of 148°–154°C at 2.5 mm Hg and was a clear viscous oil with an optical rotation of $[\alpha]_D^{25} = -19.3°$ neat (100 mm) and a density of 0.95 g/cc. The refractive index was $\eta_D^{26} = 1.4576$. Gas chromatography showed a purity greater than 99%. An elemental analysis showed: C, 59.13; H, 8.99; N, 4.12; O, 27.7. The yield was 80% of the novel compound, 1, 2:5, 6-di-O-isopropylidene-3-O-3'-(N',N'-dimethylamino-n-propyl)-D-glucofuranose.

A portion of the above oil (10 g) was hydrolyzed in aqueous sulfuric acid at a pH value of 1.9–2.1 for 10 hours with refluxing. The resulting solution was adjusted to a pH value of 4.5 with saturated $Ba(OH)_2$ solution, centrifuged, and filtered through an ultrafine filter. The filtrate was lyophillized to a white-to-slightly yellow solid having a melting point of 78°–80°C. Gas chromatography data idicated above 99% purity of the novel compound 3-O-3'-(N',N'-dimethylamino-n-propyl)-D-glucopyranose. In thin-layer chromatography, the flow rate on silica gel with a solvent mixture composed of n-propanol, ethyl acetate, $H_2O$ and $NH_3$ in the ratio by volume of 60:10:30:10, respectively, was $R_f = 0.356$.

A portion of the oil is partially hydrolyzed to 1,2-O-isopropylidene-3-O-3'-(N',N'-dimethylamino-n-propyl)-D-glucofuranose by dissolving it in distilled water and adjusting the pH of the approximately 1M solution to 3.0 ± 0.2 with 6N HCl. The solution is extracted twice with chloroform and the clear aqueous solution is refluxed for about 2 hours. Completion of the partial hydrolysis reaction was monitored by gas chromatography from disappearance of the peak of the parent compound and appearance of a new peak with a larger retention time. The solution is then cooled, made alkaline with 30% sodium hydroxide to pH 10.5 and then extracted with chloroform. The chloroform phase is separated, dried over anhydrous magnesium sulfate and vacuum distilled to remove the solvent. The resulting colorless viscous oil has an optical rotation of $[\alpha]° = -12°$[NEAT] and refractive index of 1.4687 at 25°C. Alternatively, the compound can be obtained as the hydrochloride salt by lyophillizing the aqueous solution after partial hydrolysis at pH 4.0–4.5. A white crystalline material is obtained which is recrystallized from methanol. The crystalline hydrochloride of 1,2-O-isopropylidene-3-O-3'-(N',N'-dimethylamino-n-propyl)-D-glucofuranose has a melting point of 181°–183°C and the purity as indicated by gas chromatography is 98+%. Infrared spectrophotometry indicates the presence of a strong -OH band which is not present in the parent oil. The elemental analysis for the hydrochloride salt showed: C, 49.09; H, 8.40; N, 4.14; Cl, 10.32; O, 28.12. Theoretical values are as follows: C, 49.19; H, 8.10; N, 4.09; Cl, 10.39; O, 28.11.

The gas-liquid chromatograms for the above intermediate and final novel compounds were run on a Beckman GC, Model 72-5 with a hydrogen flame detector. The column used for the intermediate novel compound was a commercially available SE-52 column, wherein methyl phenyl phenyl act as stationary phases support on Chromosorb W (H.P.) which is made by Johns-Manville Corporation. The final novel compound was chromatographed on a Chromosorb 103 glass column, which is packed with porous resins. The foregoing materials are commercially available.

EXAMPLE 2

Starting with 51 g (0.3 mole) of 4-chloro-N-methyl-piperidine hydrochloride and 26 g (0.1 mole) of 1,2:5,6-di-O-isopropylidene-D-glucofuranose and 36 g of NaOH in 150 ml 1,4-dioxane, condensation was accomplished using the general procedure outlined in Example 1. The residue remaining following vacuum distillation was dissolved and recrystallized from hot methanol. The melting point was 106°–107.5°C (sharp).

Hydrolysis of the above product in $H_2SO_4$ at a pH value of 2.1 yielded 3-O-4'-(N', methylpiperidyl)-D-glucopyranose having an optical rotation of $[\alpha]_D^{25}$ = 38°–42° in $H_2O$. A gas chromatography analysis in accordance with Example 1 indicated that the purity of the product was in excess of 96%. The melting point was 62°–65°C.

EXAMPLE 3

A solution of 0.1 mole of 1,2:5,6-di-O-isopropylidene-D-glucofuranose in 50 ml of tetrahydrofuran (THF) was added to a suspension of 0.3 mole of 2-chloro-N,N-diethylaminoethane hydrochloride and 36 g of sodium hydroxide in 100 ml of tetrahydrofuran. The suspension was mechanically stirred and refluxed overnight and the reaction mixture was treated as set out in Example 1. The desired product, 1,2:5,6-di-O-isopropylidene-3-O-2'-(N',N'-diethylaminoethyl)-D-glucofuranose was obtained as a clear yellow liquid (boiling point 144°–150°C/0.15 mm Hg) having an optical rotation of $[\alpha]_D^{28}$ = –20.6° neat and a refractive index of $\eta_C^{25}$ = 1.4532. The liquid solidified on exposure to air, probably due to formation of the carbonate salt. The yield was 85%.

Ten grams of the above product were hydrolyzed with aqueous sulfuric acid at a pH value of 1.9–2.1 for ten hours under reflux. The resulting solution was adjusted to a pH value of 4–5 with saturated barium hydroxide solution and then centrifuged and filtered. Lyophillization of the filtrate yielded 6.55g of light brown crystalline 3-O-2'-(N',N'-dietylaminoethyl)-D-glucopyranose. The optical rotation in water was $[\alpha]_D^{25}$ = +36.33°. A gas chromatography analysis in accordance with Example 1 indicated that the purity was in excess of 99%.

EXAMPLE 4

To 26 g (0.1 mole) of 1,2:5,6-di-O-isopropylidene-D-glucofuranose and 36 g (0.9 mole) of sodium hydroxide in 150 ml of refluxing tetrahydrofuran was added dropwise over one hour 0.3 mole of 3-bromopropionitrile in 50 ml of tetrahydrofuran. The reaction mixture was refluxed for an additional 6 hours and then filtered. The solids were washed with tetrahydrofuran and the washings were combined with the filtrate. The solvent was removed under reduced pressure and solid 1,2:5,6-di-O-isopropylidene-3-O-3'-propionitrile-D-glucofuranose was obtained. The decomposition point was 165°C and it was light sensitive indicating utility in photographic applications.

Five grams (0.016 mole) of the above product was dissolved in anhydrous ether and added dropwise to a suspension of 0.76 g (0.02 mole) of lithium aluminum hydride in ether. The resulting complex was dissolved in cold hydrochloric acid and neutralized rapidly with sodium bicarbonate. The suspension thus produced was extracted with chloroform and the solvent was removed to obtain a yellow oil in a yield of 250 mg. Gas chromatography in accordance with Example 1 indicated a purity of 98% and there was a sharp infrared band at 3400 $cm^{-1}$. The oil was hydrolyzed at a pH value of 2.1 in sulfuric acid and lyophillized to dryness. The yield was 85 mg of 3-O-3'-(N-propylamino)-D-glucopyranose.

EXAMPLE 5

The 3-O-2'-(N',N'-dimethylaminopropyl) derivative of 1,2:5,6-di-O-isopropylidene-D-glucofuranose was prepared by condensing 0.1 mole of 1,2:5,6-di-O-isopropylidene-D-glucofuranose with 0.3 mole of 2-chloro-N',N'-dimethylamino propane hydrochloride in the presence of 0.9 mole of sodium hydroxide in 150 ml of 1,4-dioxane. The reaction mixture was fractionally distilled under reduced pressure to obtain a yellow viscous oil (boiling point 142°–145°C/0.07 mm Hg) in 81% yield. The optical rotation was $[\alpha]_D^{25}$ = –21.5° neat and the refractive index was $\eta_D^{25}$ = 1.4549. Gas chromatography in accordance with Example 1 indicated only one component.

The above prepared yellow viscous oil (10 g) was hydrolyzed with aqueous sulfuric acid at a pH value of 2.0 by refluxing for 10 hours. The pH value of the hydrolysate was adjusted to 4–5 with saturated barium hydroxide solution, filtered and lyophillized to obtain 10.5 g of light yellow crystals of 3-O-2'-(N',N'-dimethyl-aminopropyl)-D-glucopyranose. The optical rotation in water was $[\alpha]_D^{25}$ = +37.86°. Gas chromatography in accordance with Example 1 indicated a purity in excess of 82%.

A portion of the oil, 1,2:5,6-di-O-isopropylidene-3O-2'-(N', N'-dimethylaminopropyl)-D-glucofuranose, is partially hydrolyzed at pH 3.0 ± 0.2 as indicated in Example 1. A white crystalline hydrochloride salt is obtained on lyophillization. The salt obtained is highly hygroscopic, with gas chromatographic purity being of the order of 80%.

EXAMPLE 6

To 0.1 mole of 1,2:5,6-di-O-isopropylidene-D-glucofuranose was added 0.3 mole of 2, N',N'N'-trimethylaminopropyl chloride hydrochloride along with 36 g of sodium hydroxide. The general reaction procedure was in accordance with Example 1. The oil resulting from the reaction had a boiling point of 144°–146°C at 0.6 mm Hg and a optical rotation of $[\alpha]_D^{20}$ = –20.05°neat.

The above product was hydrolyzed according to the general method outlined in Example 1 to obtain the desired 3-O-3'-(2',N',N'N'-trimethylamino-n-propyl)-D-glucopyranose. The optical rotation of the product in water was $[\alpha]_D^{20}$ = +38.0°.

A portion of the oil, 1,2:5,6-di-O-isopropylidene-3O-3'-(2',N',N'-trimethylamino-n-propyl)-D-gllucofuranose, is partially hydrolyzed at pH 3.0 + 0.2 according to the procedure mentioned in Example 1. A white crystalline 1,2-O-isopropylidene-3-O-3'-(2',N',-N'-trimethylamino-n-propyl)-D-glucofuranose hydrochloride was obtained which is highly hygroscopic in nature. Optical rotation of the hydrochloride salt at pH 7.0 and 25°C is –21.33°. Gas chromatography analysis indicated better than 99% pure major component.

EXAMPLE 7

Using the general method outlined in Example 1, 0.02 mole of 1,2:5,6O-isopropylidene-D-glucofuranose in 1,4-dioxane was reacted with 0.0225 mole of 2-(2-chloroethyl)-N-methylpyrrolidine hydrochloride and 0.0675 mole of sodium hydroxide. After 18 hours the solvent was removed and the resulting orange oil was vacuum distilled under nitrogen. The residue consisted of the desired product, 1,2:5,6-O-isopropylidene-3-O-2'-(2'-(N'-methyl)-pyrrolidyl)-ethyl-D-glucofuranose having an optical rotation of $[\alpha]_D^{25} = -22.95°$ in chloroform.

EXAMPLE 8

1,2:5,6-di-O-isopropylidene-D-glucofuranose (0.1 mole) and N-(2-chloroethyl)-pyrrolidine hydrochloride (0.15 mole) are mechanically stirred and reluxed with 0.45 mole of sodium hydroxide in 150 ml of tetrahydrofuran for 18 hours. The tetrahydrofuran is removed from the reaction products and the resulting oil is vacuum distilled under nitrogen. The 3-O-2'-(N'pyrolidyl)-ethyl)-1,2:5,6-di-O-isopropylidene-D-glucofuranose derivative has a boiling point of 165-171°C/0.15 mm Hg. Gas chromatography indicates a purity of 99%. Using the hydrolysis procedure outlined in Example 1, 10 g of the blocked oil was hydrolyzed and lyophillized giving a white hygroscopic crystalline solid.

EXAMPLE 9

The N',N'-dimethylamino-n-pentyl derivative of 1,2:5,6-di-O-isopropylidene-D-glucofuranose is made by condensing N,N-dimethylamino-n-pentyl-5-chloride hydrochloride with 1,2:5,6-di-O-isopropylidene-D-glucofuranose in the presence of pulverized sodium hydroxide in freshly purified, dry 1,4-dioxane as described in procedure in Example 1. The product was confirmed by gas chromatography and infrared spectra.

N,N-dimethylamino-n-pentyl chloride hydrochloride is made from commercially available sample of N,N-dimethylamino-n-pentyl alcohol by treatment with thionyl chloride (SOCl$_2$). Specifically, 10.7 g of thionyl chloride in a 250 ml three neck round bottom flask is cooled in a salt-ice water bath and stirred vigorously. To the cooled solution is added, dropwise, 10 g of N,N-dimethylamino-n-pentyl alcohol. The reaction is exothermic and temperature is carefully controlled. The mixture is stirred for one hour after the evolution of SO$_2$ and HCl subsides. The mixture is brought to room temperature and allowed to stir overnight. Absolute alcohol is added to destroy excess thionyl chloride. Ten grams of crude N,N-dimethylamino-n-pentyl chloride hydrochloride is obtained as a while solid. This is used directly for the condensation reaction with 1,2:5,6-di-O-isopropylidene-D-glucofuranose without further purification. The alcohol and chloride can be resolved on Chromosorb 103 gas chromatography column.

EXAMPLE 10

Bromine (9.8 g) was added slowly and dropwise to a mechanically stirred mixture of 50 g cracked ice and a chilled aqueous sodium hydroxide solution (7 g/20 ml water). After the addition of bromine is complete, 15 g of 1,2:5,6-di-O-isopropylidene-3-O-acetamido-D-glucofuranose (prepared by the general procedure outlined in Example 1 by the condensation of 1,2:5,6-di-O-isopropylidene-D-glucofuranose with 2-chloroacetamide in the presence of sodium hydroxide) is added in four portions 15 minutes apart. The reaction mixture is heated for 1 hour in a water bath. After this time an additional aqueous solution of sodium hydroxide (20 g/20 ml) is added and heating is continued for another hour. The mixture is cooled and extracted 3 times with ether. The ether extract is dried over anhydrous magnesium sulfate. The yellow hygroscropic solid remaining after evaporating off the ether is the desired 1,2:5,6-di-O-isopropylidene-3-O-aminomethyl-D-glucofuranose derivative. The product was identified by the disappearance of the carbonyl stretching at 1670 cm$^{-1}$ found in the parent acetamido compound.

EXAMPLE 11

A solution of 26.0 g of 1,2:3, 4-di-O-isopropylidene-D-galactopyranose in 50 ml of anhydrous tetrahydrofuran (THF) was mixed with a suspension of 0.3 mole of 3-chloro-N,N-dimethyl-amino propane hydrochloride and 36 g of sodium hydroxide in 100 ml THF. The mixture was stirred vigorously and refluxed for 3 hours. The resulting brownish solution was cooled, filtered and most of the solvent was evaporated leaving a brown oil. The remaining solvent and unreacted 3-chloro-N,N-dimethylamino propane were removed by fractional distillation under reduced pressure. The residual oil was extracted with chloroform, decolorized with activated charcoal and dried over anhydrous magnesium sulfate. Removal of the chloroform solvent yielded 13.4 g of yellow oil, which was identified as 1,2:3,4-di-O-isopropylidene-6-O-3'-(N',N'-dimethylamino-n-propyl)-D-galactopyranose. Infrared and gas chromatography in accordance with Example 1 indicated the presence of one major component having a refractive index of $\eta_D^{28} = 1.461$ and an optical rotation of $[\alpha]_D^{25} = -49.4°$ in chloroform The oil was refluxed with 50 ml of 0.5 N sulfuric acid for 18 hours. The resulting solution was washed with chloroform and the pH value was adjusted to 4.2. On lyophillization, the aqueous solution yielded 4.67 g of white crystalline solid 6-O-3'-(N',N'-dimethylamino-n-propyl)-D-galactopyranose having an optical rotation of $[\alpha]_D^{25} = +77.2°$ in H$_2$O. A gas chromatography analysis in accordance with Example 1 indicated that the purity of the product was in excess of 95%.

EXAMPLE 12

This example illustrates the preparation of 6O-2'-(N',N'-dimethylaminopropyl)-D-galactose.

The general procedure of Example 2 was followed with the exception of using 2-chloro-N,N-dimethylaminopropane hydrochloride as a starting material rather than the corresponding 3-chloro derivative. The intermediate product had an optical rotation in water of $[\alpha]_D^{24} = -54.5°$, and a refractive index of $\eta_D^{24} = 1.4552$. The final product had a rate of flow value on thin layer chromatography analysis in accordance with Example 1 R$_f$ = 0.376.

EXAMPLE 13

α-N,N-dimethylaminoisopropyl-D-glucoside was prepared by starting with 0.1 mole of anhydrous D-glucose inn 300 ml of THF and adding 0.3 mole of N,N-dimethylamino2-propanol along with 95 g of dry Dowex 50-X cation exchange resin in H⁺ form. The reaction mixture was refluxed for 18 hours and then 70 ml of 5 N ammonium hydroxide was added. The reaction mixture was filtered and the filtrate was concentrated under reduced pressure to obtain a brown viscous oil. The oil was dissolved in hot ethanol, decolorized with charcoal, dried with anhydrous $MgSO_4$, and acidified with dry HCl gas. The ethanol solution was concentrated from 500 ml to approximately 100 ml and allowed to cool under running tap water. The α-N,N-dimethylaminoisopropyl-D-glucoside product crystallized from the concentrated solution upon scratching the container. Thin layer chromatography in accordance with Example 1 indicated a flow rate on silica gel of $R_f = 0.34$.

EXAMPLE 14

Evaluation was carried out on the capacity of 3-O-3'-(N',N'-dimethylamino-n-propyl)-D-glucose to affect the rate of learning of tasks by normal 2 month old albino rats. The tasks involved the selection of the appropriate area within a learning box to which to advance in order to avoid being shocked by current passed through the grid floor of the cage. The rats were cued by the appearance of a light in the appropriate chamber.

In the first group of studies, the rats were given one trial on each of 4 days before, and three trials on each of 3 days after, the initiation of treatment with either the drug or a placebo. The drug was given intraperitoneally daily after trails at the rate of 100 mg/kg of body weight. The eight rats which were to receive the placebo performed the correct avoidance response during the control period on 52.5% of the trials and the eight rats which were to receive the drug, i.e., 3-O-3'-(N',N'-dimethylamino-n-propyl)-D-glucose, performed the correct avoidance response during the control period on 42.5% of trials. During the period of the drug or placebo administration, the performance of the control rats deteriorated, falling from 52.5% to 36.6% of successes; while the success rate for the rats receiving the 3-O-3'-(N',N'-dimethylamino-n-propyl)-D-glucose rose from 42.5% to 90%. The effects of the drug on learning in this experiment were statistically significant at $P \leq 0.02$. The same rats were examined for their tendency to explore the open field during the control and drug treatment periods. The drug was found to have no effect on this measure of the curiosity and mobility of the rats in the absence of a specific learning situation.

In a second group of studies, the rats were given 30 trials per day and the drug or placebo solution was administered daily after trials starting on Day 1. Scorings of the avoidance successes during blocks of 10 consecutive trials were made and successful learning was defined as the achievement of 7 out of 10 consecutive successful avoidance responses within 500 trials. Several rats failed to reach this criterion and were discarded. The rats which were given placebo solution after trials reached criterion in 148.4 ± 25 trials, while the rats given the 3-O-3'-(N',N'-dimethylamino-n-propyl)-D-glucose reached criterion in 70.3 ± 6.9 trials. These results indicate that the rats given the drug learned to successfully avoid foot shock at a rate that was more than twice as rapid as that of the rats receiving the placebo. As established by the prior art, aged rats over 2 years old exhibit memory deficiency for learning. In a further study, normal aged rats between 24 and 28 months of age are required to learn to avoid receiving shock to the feet by jumping to a safety shelf that is partially obscured. Rats under 16 months of age remember the location of the shelf 24 hours after the first success when no other learning trials are interposed. Rats 24 months of age and older do not. However, rats 24–28 months of age given 50 mg/kg of body weight of 3-O-3'-(N',N' -dimethylamino-n-propyl)-D-glucose 24 hours after the initial learning experience, which terminates with the first success, do remember the location of the safety shelf and jump to it before being shocked another time. Control aged animals fail to recall the location of the safety shelf and drug-treated aged animals succeed in this recall on the first trial after the 24-hour gap. Thus, error frequency is reduced by more than 90%. The results indicate that 3-O-3'-(N',N'-dimethylamino-n-propyl)-D-glucose restores aspects of rat memory function that have deteriorated with aging.

EXAMPLE 15

This example evaluates the effect of 1,2-O-isopropylidene-3-O-3'-(N',N'-dimethylamino-n-propyl)-D-glucofuranose hydrochloride on the learning of a group of tasks by normal 2 month old albino rats. The tasks involve the selection of the appropriate area within a learning box to which to advance in order to avoid being shocked by current passed through the grid floor of the cage. The rats are cued by the appearance of a light in the appropriate chamber.

In the first group of studies, the rats are given one trial on each of 4 days before, and three trials on each of 3 days after, the initiation of treatment with either the drug or a placebo. The drug is given intraperitoneally daily after trials at 100 mg/kg of body weight. During the control period the rats perform the correct avoidance response on approximately 50% of trials. The performance of the rats receiving a placebo is not changed but rats receiving the drug achieve correct avoidance responses on more than 90% of the trials. The drug has no effect on the tendency of the rats to explore the open field (a measure of animal curiosity and mobility) in the absence of a specific learning situation.

In a second group of studies, rats are given 30 trials per day and the 1,2-O-isopropylidene-3-O-3'-(N',N'-dimethylamino-n-propyl)-D-glucofuranose hydrochloride or a placebo solution is administered daily after trials starting on Day 1. Scorings of the avoidance successes during blocks of 10 consecutive trials are made and successful learning is defined as the achievement of 7 out of 10 consecutive successful avoidance responses within 500 trials. The rats failing to reach criterion within 500 trials are discarded. The rats receiving the 1,2-O-isopropylidene-3-O-3'-(N',N',-dimethylamino-n-propyl)-D-gluco-furanose hydrochloride reach criterion approximately twice as fast as those receiving the placebo.

As established by the prior art, aged rats over 2 years old exhibit memory deficiency for learning. In a further study normal aged rats between 24 and 28 months of age are required to learn to avoid receiving shock to the feet by jumping to a safety shelf that is partially obscured. Rats under 16 months of age remember the location of the shelf 24 hours after the first success when no other learning trials are interposed. Rats 24 months and older do not. However, rats 24–28 months of age given 50 mg/kg of body weight of 1,2-O-isopropylidene-3-O-3'-(N',N'-dimethylamino-n-propyl)-D-glucofuranose hydrochloride 24 hours after the initial learning experience, which terminates with the first success, do remember the location of the safety shelf and jump to it before being shocked another time. The results show categorically that control aged rats fail to recall the location of the safety shelf, whereas drug-treated rats succeed in this recall on the first trial after the 24-hour gap. Error frequency is reduced by more than 90%. The results indicate that 1,2-O-isopropylidene-3-O-3'-(N',N'-dimethylamino-n-propyl)-D-glucofuranose hydrochloride restores aspects of rat memory function that have deteriorated with aging.

I claim:
1. A method of enhancing learning or memory in a warm blooded animal which consists essentially of administering thereto a therapeutically effective amount to enhance the ability of the animal to learn tasks or to enhance the ability of the animal to memorize information of a substance selected from the group consisting of
  I. ethereally monosubstituted monosaccharides having the formula $S_1$—O—Y and therapeutically effective and pharmaceutically acceptable organic acid and inorganic acid salts thereof, and
  II. ethereal monosubstitutions of monosaccharide derivatives having the formula $S_2$—O—Y and therapeutically effective and pharmaceutically acceptable organic acid and inorganic acid salts thereof, Wherein:
    1. $S_1$ is the residue of a non-derivatized monosaccharide selected from the group consisting of pentoses, hexoses and heptoses,
    2. $S_2$ is the residue of a monosaccharide selected from the group consisting of pentoses, hexoses and heptoses which has been derivatized with a substance selected from the group consisting of (a) an aliphatic alcohol containing 1–18 carbon atoms to produce an acetal group at the site of an available hydroxyl residue, (b) an aldehyde containing 1–18 carbon atoms to produce an acetal group at the site of an available hydroxyl residue, (c) a ketone containing 1–18 carbon atoms to produce a ketal group at the site of an available hydroxyl residue, and (d) an organic acid residue containing 1–18 carbon atoms to produce an ester group at the site of an available hydroxyl residue, and
    3. Y in each instance is selected from the group consisting of cyclic monovalent nitrogen containing organic radicals and residua and monovalent organic radicals and residua having the general formula

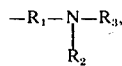

wherein $R_1$ is a divalent organic radical having a linear carbon chain length of about 1–7 carbon atoms and $R_2$ and $R_3$ are selected from the group consisting of —H, —OH, —SH, halogen and monovalent organic radicals and residua having a linear carbon chain length of about 1–7 carbon atoms,
and subjecting the said warm blooded animal to an environment wherein it is required to learn tasks or memorize information.

2. The method of claim 1 wherein Y is

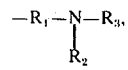

$R_1$ is a hydrocarbon radical having a linear carbon chain length of 1–3 carbon atoms, and $R_2$ and $R_3$ are selected from the group consisting of hydrogen and hydrocarbon radicals having a linear carbon chain length of 1–3 carbon atoms.

3. The method of claim 1 wherein Y is selected from the group consisting of
  -(n-propylamino),
  -(N',N'-dimethylamino-n-propyl),
  -(N',N'-dimethylaminoisopropyl),
  -(N-methyl piperidyl),
  -(N',N'-dimethylaminoethyl),
  -(N',N'-diethylaminoethyl), and
  -(2',N',N'-trimethylamino-n-propyl).

4. The method of claim 1 wherein Y is -(N',N'-dimethylamino-n-propyl).

5. The method of claim 1 wherein the said ethereally monosubstituted monosaccharide $S_1$—O—Y has the formula

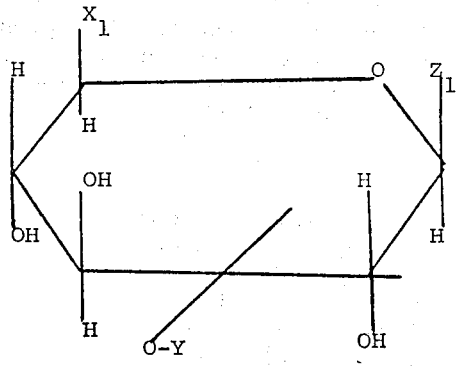

wherein $X_1$ and $Z_1$ are selected from the group consisting of H, OH and hydroxyalkyl groups containing up to 2 carbon atoms, Y represents the same organic radicals and residua as set out in claim 1, and one of the OH groups, $X_1$ or $Z_1$ in said formula is replaced by —O—Y.

6. The method of claim 5 wherein Y is

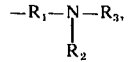

$R_1$ is a hydrocarbon radical having a linear carbon chain length of 1–3 carbon atoms, and $R_2$ and $R_3$ are selected from the group consisting of hydrogen and hydrocarbon radicals having a linear carbon chain length of 1–3 carbon atoms.

7. The method of claim 5 wherein the said monosaccharide is a hexose.

8. The method of claim 7 wherein Y is

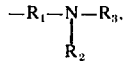

$R_1$ is a hydrocarbon radical having a linear carbon chain length of 1–3 carbon atoms, and $R_2$ and $R_3$ are selected from the group consisting of hydrogen and hydrocarbon radicals having a linear carbon chain length of 1–3 carbon atoms.

9. The method of claim 7 wherein Y is selected from the group consisting of
-(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

10. The method of claim 9 wherein Y is -(N',N'-dimethylamino-n-propyl).

11. The method of claim 5 wherein the said monosaccharide is selected from the group consisting of glucose and galactose.

12. The method of claim 11 wherein the glucose is monosubstituted in the 1-O- or 3-O- position and the galactose is monosubstituted in the 6-O-position.

13. The method of claim 12 wherein Y is

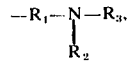

$R_1$ is a hydrocarbon radical having a linear carbon chain length of 1–3 carbon atoms and $R_2$ and $R_3$ are selected from the group consisting of hydrogen and hydrocarbon radicals having a linear carbon chain length of 1–3 carbon atoms.

14. The method of claim 12 wherein Y is selected from the group consisting of
-(n-propylamino),
-(N',N'-dimethylamino-n-propyl),
-(N',N'-dimethylaminoisopropyl),
-(N-methyl piperidyl),
(N',N'-dimethylaminoethyl),
-(N',N'-diethylaminoethyl), and
-(2',N',N'-trimethylamino-n-propyl).

15. The method of claim 12 wherein Y is -(N',N'-dimethylamino-n-propyl).

16. The method of claim 11 wherein the monosubstituted monosaccharide is selected from the group consisting of
3-O-3'-(n-propylamino)-D-glucose,
3-O-3'-(N',N'-dimethylamino-n-propyl)-D-glucose,
3-O-4'-(N-methyl piperidyl)-D-glucose,
3-O-2'-(N',N'-dimethylaminoethyl)-D-glucose,
3-O-2'-(N',N'-diethylaminoethyl)-D-glucose,
3-O-3'-(2',N',N'-trimethylamino-n-propyl)-D-glucose,
α-N',N'-dimethylaminoisopropyl-D-glucoside,
6-O-3'-(N',N'-dimethylamino-n-propyl)-D-galactose,
3-O-2'-(N',N'-dimethylaminopropyl)-D-glucose,
6-O-2'-(N',N'-dimethylaminopropyl)-D-galactose,
and therapeutically effective and pharmaceutically acceptable organic and inorganic acid salts thereof.

17. The method of claim 11 wherein the monosubstituted monosaccharide is 3-O-3'-(N',N'-dimethylamino-n-propyl)-D-glucose, or a therapeutically effective and pharmaceutically acceptable organic acid or inorganic acid salt thereof.

18. The method of claim 1 wherein the said ethereal monosubstitution of the monosaccharide derivative $S_2$—O—Y has a formula selected from the group consisting of:

(a)

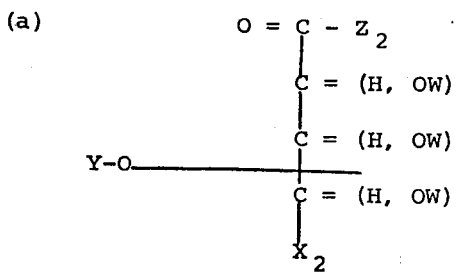

(b)

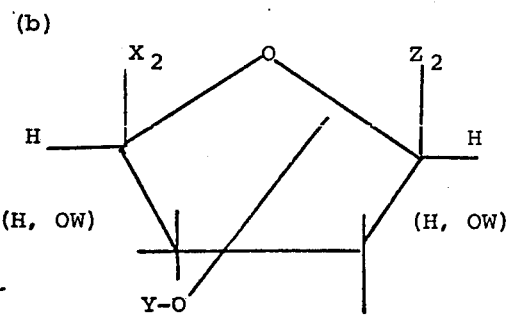

and (c)

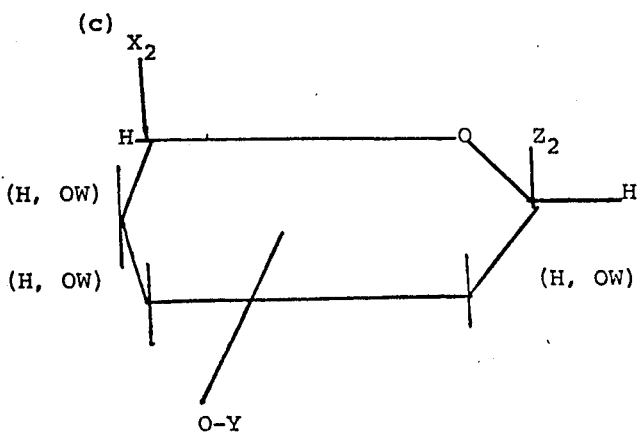

wherein $X_2$ and $Z_2$ are selected from the group consisting of H, OH, and monovalent hydroxyalkyl, alkoxyl and alkoxyalkyl radicals containing up to 3 carbon atoms, W is selected from the group consisting of H and monovalent alkyl, alkenyl, cyclic alkane, cyclic aromatic, and acyl radicals containing 1–18 carbon atoms, Y represents the same organic radicals and residua as set out in claim 1, and one of the OH groups, $X_2$ or $Z_2$ in said formulae is replaced by —O—Y.

19. The method of claim 18 wherein the said monosaccharide is a hexose.

20. The method of claim 19 wherein Y is

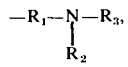

$R_1$ is a hydrocarbon radical having a linear carbon chain length of 1–3 carbon atoms, and $R_2$ and $R_3$ are selected from the group consisting of hydrogen and hydrocarbon radicals having a linear carbon chain length of 1–3 carbon atoms.

21. The method of claim 19 wherein Y is selected from the group consisting of
-(n-propylamino),
-(N',N'-dimethylamino-n-propyl),
-(N',N'-dimethylamino isopropyl),
-(N-methyl piperidyl),
-(N',N'-dimethylaminoethyl),
-(N',N'-diethylaminoethyl), and
-(2',N',N'-trimethylamino-n-propyl).

22. The method of claim 19 wherein Y is -(N',N'-dimethylamino-n-propyl).

23. The method of claim 18 wherein the said monosaccharide is selected from the group consisting of glucose and galactose.

24. The method of claim 23 wherein the glucose is monosubstituted in the 1-O- or 3-O-position and the galactose is monosubstituted in the 6-O- position.

25. The method of claim 24 wherein Y is

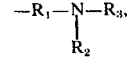

$R_1$ is a hydrocarbon radical having a linear carbon chain length of 1–3 carbon atoms and $R_2$ and $R_3$ are selected from the group consisting of hydrogen and hydrocarbon radicals having a linear carbon chain length of 1–3 carbon atoms.

26. The method of claim 24 wherein Y is selected from the group consisting of
-(n-propylamino),
-(N',N'-dimethylamino-n-propyl),
-(N',N'-dimethylaminoisopropyl),
-(N-methyl piperidyl),
-(N',N'-dimethylaminoethyl),
-(N,N'-diethylaminoethyl), and
-(2',N',N'-trimethylamino-n-propyl).

27. The method of claim 24 wherein Y is -(N',N'-dimethylamino-n-propyl).

28. The method of claim 23 wherein the said ethereal monosubstitution of the monosaccharide derivative is 3-O-3'-(N',N'-dimethylamino-n-propyl)-1,2-O-isopropylidene-D-glucofuranose, or a therapeutically effective and pharmaceutically acceptable organic acid or inorganic acid salt thereof.

29. The method of claim 1 wherein the said substance is in the form of a salt of an acid selected from the group consisting of HCl, HBr, $H_2SO_4$, $HNO_3$, benzoic acid, p-aminobenzoic acid, p-acetamidobenzoi acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

30. The method of claim 29 wherein the said substance is 3-O-3'-(N',N'-dimethylamino-n-propyl)-D-glucose.

31. The method of claim 30 wherein the said acid is HCl.

32. The method of claim 29 wherein the said substance is 3-O-3'-(N',N'-dimethylamino-n-propyl)-1,2-O-isopropylidene-D-glucofuranose.

33. The method of claim 32 wherein the said acid is HCl.

34. The method of claim 23 wherein the said ethereal monosubstitution of the monosaccharide derivative is selected from the group consisting of
3-O-3'-(N',N'-dimethylamino-n-propyl)-1, 2-O-isopropylidene-D-glucofuranose,
3-O-4(N'-methylpiperidyl)-1,2-O-isopropylidene-D-glucofuranose,
3-O-2'-(N',N'-dimethylaminoethyl)-1,2-O-isopropylidene-D-glucofuranose,
3-O-3'-(2',N',N'-trimethylamino-n-propyl)-1, 2-O-isopropylidene-D-glucofuranose,
3-O-2'-(N',N'-dimethylaminopropyl)-1, 2-O-isopropylidene-D-glucofuranose,
6-O-3'-(N',N'-dimethylamino-n-propyl)-1, 2-O-isopropylidene-D-galactopyranose,
6-O-2'-(N',N'-dimethylaminopropyl)-1, 2-O-isopropylidene-D-galactopyranose,
3-O-3'-(N',N'-dimethylamino-n-propyl)-1, 2:5,6-di-O-isopropylidene-D-glucofuranose,
3-O-4'-(N'-methylpiperidyl)-1,2:5, 6-di-O-isopropylidene-D-glucofuranose,
3-O-2'-(N',N'-dimethylaminoethyl)-1,2:5, 6-di-O-isopropylidene-D-glucofuranose,
3-O-3'-(2',N',N'-trimethylamino-n-propyl)-1,2:5,6-di-O-isopropylidene-D-glucofuranose,
3-O-2'-(N',N'-dimethylaminopropyl)-1 2:5, 6-di-O-isopropylidene-D-glucofuranose,
6-O-3'-(N',N'-dimethylamino-n-propyl)-1 2:3,4-di-O-isopropylidene-D-galactopyranose,
6-O-2'-(N',N'-dimethylaminopropyl)-1, 2:3, 4-di-O-isopropylidene-D-galactopyranose,
α-N',N'-dimethylaminoisopropyl-2, 3:5, 6-di-O-isopropylidene-D-glucofuranoside,
and therapeutically effective and pharmaceutically acceptable organic and inorganic acid salts thereof.

* * * * *